US011234691B2

(12) United States Patent
Vailhe et al.

(10) Patent No.: US 11,234,691 B2
(45) Date of Patent: Feb. 1, 2022

(54) COMPOSITE SUTURE NEEDLES HAVING ROTATABLE SECTIONS

(71) Applicant: Ethicon, Inc., Somerville, NJ (US)

(72) Inventors: Christophe Vailhe, Hillsborough, NJ (US); Robert J. Tannhauser, Bridgewater, NJ (US); Leo B. Kriksunov, Ithaca, NY (US)

(73) Assignee: Ethicon, Inc., Somerville, NJ (US)

( * ) Notice: Subject to any disclaimer, the term of this patent is extended or adjusted under 35 U.S.C. 154(b) by 164 days.

(21) Appl. No.: 16/539,086

(22) Filed: Aug. 13, 2019

(65) Prior Publication Data

US 2021/0045741 A1    Feb. 18, 2021

(51) Int. Cl.
*A61B 17/06*  (2006.01)
*A61B 17/34*  (2006.01)

(52) U.S. Cl.
CPC .. *A61B 17/06066* (2013.01); *A61B 17/06004* (2013.01); *A61B 17/3403* (2013.01); *A61B 17/3478* (2013.01); *A61B 2017/0609* (2013.01)

(58) Field of Classification Search
CPC .............. A61B 17/06; A61B 17/06066; A61B 17/3478; A61B 2017/061; A61B 2017/06104; A61B 2017/0609; A61B 2017/06052

See application file for complete search history.

(56) References Cited

U.S. PATENT DOCUMENTS

| 2,869,550 A | 1/1959 | Kurtz |
| 3,094,123 A | 6/1963 | Kurtz |
| 3,197,997 A | 8/1965 | Kurtz |

(Continued)

FOREIGN PATENT DOCUMENTS

| CH | 597835 | 4/1978 |
| DE | 3223153 | 11/1983 |

(Continued)

OTHER PUBLICATIONS

Scali, M., Pusch, T. P., Breedveld, P., & Dodou, D. (2017). Needle-like instruments for steering through solid organs: A review of the scientific and patent literature. Institution of Mechanical Engineers. Proceedings. Part H: Journal of Engineering in Medicine, 231(3), 250-265. DOI: 10.1177/0954411916672149.

(Continued)

*Primary Examiner* — Tuan V Nguyen (57) ABSTRACT

A reconfigurable suture needle includes an elongated body having a curved proximal section and a curved distal section. A joint interconnects a distal end of the curved proximal section and a proximal end of the curved distal section. The joint enables the curved proximal section and the curved distal section to rotate relative to one another between a first configuration having a higher profile and a second configuration having a lower profile. Each of the curved proximal and distal sections of the elongated body defines about one-quarter of a circle. The elongated body has a semi-circular shape when in the first configuration and a wave shape when in the second configuration. The elongated body is rotated into the smaller profile for passing through a cannula and, after passing through the cannula, rotated back into the higher profile for use as a suturing needle.

20 Claims, 8 Drawing Sheets

(56) References Cited

U.S. PATENT DOCUMENTS

| | | | |
|---|---|---|---|
| 3,249,104 | A | 5/1966 | Hohnstein |
| 4,140,125 | A | 2/1979 | Smith |
| 5,041,127 | A | 8/1991 | Troutman |
| 5,269,806 | A | 12/1993 | Sardelis |
| 5,382,257 | A | 1/1995 | Lewis et al. |
| 5,649,961 | A | 7/1997 | McGregor |
| 5,683,415 | A | 11/1997 | Brunken |
| 5,683,416 | A | 11/1997 | McGregor |
| 5,741,299 | A | 4/1998 | Rudt |
| 5,797,961 | A | 8/1998 | Smith |
| 5,853,423 | A | 12/1998 | McGregor |
| 5,897,572 | A | 4/1999 | Schulsinger |
| D492,778 | S | 7/2004 | Narini |
| 9,393,012 | B2 | 7/2016 | DiPiero |
| 9,433,409 | B2 | 9/2016 | Nose |
| D895,114 | S | 9/2020 | Cichocki |
| 2007/0135838 | A1 | 6/2007 | Meyer |
| 2007/0219586 | A1 | 9/2007 | Mahadevan |
| 2008/0306496 | A1* | 12/2008 | Regner .............. A61B 17/0643 606/151 |
| 2010/0100125 | A1 | 4/2010 | Mahadevan |
| 2011/0301642 | A1 | 12/2011 | White et al. |
| 2012/0158049 | A1 | 6/2012 | Kato |
| 2013/0023725 | A1 | 1/2013 | Nose et al. |
| 2014/0005719 | A1 | 1/2014 | Uetake |
| 2015/0142018 | A1 | 5/2015 | Sniffin et al. |
| 2015/0142040 | A1 | 5/2015 | Kawaura et al. |
| 2020/0268375 | A1 | 8/2020 | Cichocki |
| 2020/0268378 | A1* | 8/2020 | Cichocki, Jr. ...... A61B 17/0469 |
| 2020/0268379 | A1 | 8/2020 | Cichocki |
| 2020/0268382 | A1 | 8/2020 | Vailhe |
| 2020/0268383 | A1 | 8/2020 | Vailhe |

FOREIGN PATENT DOCUMENTS

| | | |
|---|---|---|
| EP | 3431014 | 1/2019 |
| WO | 2006027549 | 3/2006 |

OTHER PUBLICATIONS

Di Qi, Karthikeyan Panneerselvama, Woojin Ahnb, Venkata Arikatlac, Andinet Enquobahriec, & Suvranu Dea. Virtual Interactive Suturing for the Fundamentals of Laparoscopic Surgery (FLS). Journal of Biomedical Informatics 75, Nov. 2017, pp. 48-62.

International Search Report issued in counterpart foreign application International Application No. PCT/IB2020/057512, dated Nov. 4, 2020, 8 pages.

* cited by examiner

COMPOSITE SUTURE NEEDLES HAVING ROTATABLE SECTIONS

BACKGROUND OF THE INVENTION

Field of the Invention

The present patent application is generally related to surgical procedures and surgical tools, and is more specifically related to suture needles used for suturing tissue.

Description of the Related Art

Surgeons typically use cannulas and trocars to position surgical tools, such as suture needles, at surgical sites. The size of a suture needle that can be passed through the cannula to a surgical site is limited by the size of the opening in the cannula. In many instances, surgeons desire to use larger curved needles for closing surgical wounds and repairing anatomical features, however, passing the larger needles through smaller trocars is difficult. For example, 5 mm trocars are often used during minimally invasive surgeries (MIS), however, surgeons cannot pass the larger curved suture needles (e.g., suture needles having a height of 10-13 mm) through the 5 mm trocars so they are forced to use only smaller suture needles.

The smaller suture needles are less than optimal because, inter alia, they often require a surgeon to make many more passes of the suture needle and suture thread through tissue, which lengthens the surgical procedure and can frustrate the surgeon. Using smaller needles may also produce a bite distance that puts the wound or anatomical feature at risk of dehiscence.

In addition, larger-sized suture threads cannot be easily attached to the smaller suture needles. Thus, when fine sutures are passed through tissue with a smaller bite size, a cheese wire effect may result, whereby the suture cuts through the tissue it is intended to hold.

Thus, there is a need for improved suture needles that may be passed through relatively smaller trocars (e.g., 5 mm trocars) that are used in surgical procedures. There is also a need for systems, devices and methods for passing larger suture needles through relatively smaller trocars.

SUMMARY OF THE INVENTION

In one embodiment, a suture needle preferably includes an elongated body having a joint that enables sections of the suture needle to be rotated relative to one another for reconfiguring the suture needle from a high-profile configuration (e.g., a semi-circular configuration, a half-circle configuration) to a low-profile configuration (e.g., a wave-shaped configuration, a sine wave-shaped configuration) for being passed through cannulas used during surgical procedures. The types of cannulas that may be used include but are not limited to hollow conduits, trocars, body cavity access ports, MIS conduits, surgical ports, trocar ports, access cannulas, and/or surgical access channels. In one embodiment, the cannula may be a small trocar (e.g., a 5 mm trocar, a 6 mm trocar, an 8 mm trocar, a 10 mm trocar, or similar device). In one embodiment, after the suture needle having the low-profile configuration is passed through the cannula (e.g., a trocar) to a surgical site, the suture needle may be rotated back into the high-profile configuration for being used as a suture needle to perform a suturing operation. At the end of a suturing operation, the suture needle may be rotated back into the low-profile configuration for removing the suture needle through the cannula.

As used is the present patent application, the term cannula is defined as meaning surgical devices used for introducing surgical tools (e.g., suture needles) into surgical sites including but not limited to trocars, hollow conduits, body cavity access ports, MIS conduits, surgical ports, trocar ports, access cannulas, and/or surgical access channels. In one embodiment, the terms cannula and trocar may be used interchangeably.

In one embodiment, larger needles (e.g., CTX sized needles) having a rotatable joint may be passed through a small 5 mm trocar. Enabling the use of larger needles through smaller trocars preferably results in many benefits including the option to use any trocar positioned at any location during surgery since the needles will work with 5 mm, 8 mm, 10 mm, and 12 mm standard trocars. Moreover, smaller incisions associated with 5 mm trocar ports make the trocar port wound much easier to close and provides the patient with many benefits including 1) lower risk of incisional hernia, 2) better cosmesis, 3) less pain, and 4) lower risk of infection.

In one embodiment, a reconfigurable suture needle for use in minimally invasive surgeries (MIS) and robotic surgery applications is preferably moveable (e.g., rotatable) between a higher profile configuration for use as a suturing needle and a lower profile configuration for being passable through small diameter trocars (e.g., a 5 mm trocar). In one embodiment, the reconfigurable suture needle may have a semi-circular shape when in the higher profile configuration and a wave-shaped configuration when in lower profile configuration. In one embodiment, when the reconfigurable suture needle is in the higher profile configuration, it has a height and/or dimension that larger than an inner diameter of a conduit of a small trocar. Thus, the suture needle is reconfigured into the lower profile configuration to have a height and/or dimension that is less than or equal to the inner diameter of the conduit of the small trocar for being passable through the small trocar. Once the suture needle (in the lower profile configuration) has been passed through the trocar, it may be transformed back into the higher profile configuration for use as a suture needle.

In one embodiment, a suture needle preferably has an elongated body with two or more sections that are interconnected by a rotatable joint. The joint enables the two or more sections to be selectively rotated into the lower profile configuration for delivering the elongated body through a trocar. Once the two or more sections are delivered through the trocar, the sections may be rotated into a semi-circular shape so that the elongated body may be used as a suturing needle for suturing tissue.

In one embodiment, the joint preferably enables the sections of the elongated body to be rotated relative to one another into one or more stable positions. In one embodiment, the joint may have a first stable position in which the elongated body of the suture needle has a semi-circular shape and a second stable position in which the elongated body of the suture needle has a wave shape (e.g., a sine wave configuration). The joint may generate audible sounds (e.g., a clicking sound) or tactile feedback to provide surgical personnel with an indication of whether the suture needle is in the higher profile, semi-circular shaped configuration or the lower profile, wave-shaped configuration.

In one embodiment, the joint and/or the rotatable sections of the elongated body may include threads for enabling tightening. In one embodiment, the threads are loosened when the sections of the elongated body are rotated into the lower profile, wave-shaped configuration. In one embodiment, the threads are tightened when the sections of the elongated body are rotated into the higher profile, semi-circular shaped configuration, which enhances the stability and structural integrity of the suture needle as it is used for suturing tissue.

In one embodiment, the joint may interconnect opposing ends of two sections of an elongated body of a reconfigurable suture needle. In one embodiment, an end of a first section may include a post projecting therefrom that has an oval-shaped cross-section, and an opposing end of a second section may include a post opening having an oval-shaped cross-section that is adapted to receive the post having the oval-shaped cross-section. In one embodiment, rotating the two sections of the elongated body about the joint may result in the formation of a friction fit or tightening between the outer surface of the post having the oval-shaped cross-section and the inner surface of the post opening having the oval-shaped cross-section for holding the elongated body of the suture needle in a stable position. In one embodiment, the friction fit or tightening between the post having the oval-shaped cross-section and the post opening having the oval-shaped cross-section may occur when the sections of the elongates body of the suture needle are rotated into the higher profile, semi-circular shaped configuration. In one embodiment, the free end of the post may have a swaged or bulbous end for coupling the post with the post opening and/or preventing the post from separating from the post opening.

In one embodiment, a reconfigurable suture needle preferably includes an elongated body having two or more curved sections that are interconnected with one another by a rotatable joint. In one embodiment, a first section of the elongated body desirably includes a sharp end (e.g., a needle point) and an opposing connecting end, and a second section of the elongated body desirably has a joining end and an opposing suture engaging end with a suture attached thereto.

In one embodiment, the first and second sections are rotatably connected to each other at the connecting end and the joining end of the respective first and second sections.

In one embodiment, the sections are configured to be immobilized when forming a semi-circular shape.

In one embodiment, the rotatable connection for the sections may be threaded or swaged.

In one embodiment, the rotatable connection is preferably tightened when the elongated body of the suture needle has a semi-circular shape.

In one embodiment, the connecting end and the joining end of the sections may include a plug/receptacle connector or a male/female connector.

In one embodiment, the connecting end and the joining end of the sections may engage one another through an interposer connector, which is connected to each section.

In one embodiment, a reconfigurable suture needle may include a sleeve that is configured to fit (e.g., slide) over a rotatable connection (e.g., a rotatable joint) to further immobilize, reinforce, and/or stabilize the connection of the connecting end and joining end of the opposing sections of the elongated body of the suture needle.

In one embodiment, a reconfigurable suture needle may include one or more grooves, slits, and/or ridges for aligning and immobilizing the elongated body of the suture needle in either the higher profile, semi-circular shaped configuration or the lower profile, wave-shaped configuration.

In one embodiment, a reconfigurable suture needle preferably includes an elongated body having a curved proximal section with a suture attachment end (e.g., a suture attachment hole) and a curved distal section with a tissue penetrating end (e.g., a needle point, a sharpened tip). In one embodiment, a joint interconnects a distal end of the curved proximal section and a proximal end of the curved distal section. In one embodiment, the joint desirably enables the curved proximal section and the curved distal section to rotate relative to one another for transforming the elongated body of the suture needle between a first configuration having a higher profile and a second configuration having a lower profile.

In one embodiment, the elongated body of the suture needle preferably has a greater height (e.g., 10-13 mm) when in the first, high-profile configuration and a smaller height (e.g., 5 mm or less) when in the second, low-profile configuration.

In one embodiment, each of the curved proximal and distal sections of the elongated body preferably defines a section having a shape that is about one-quarter (¼) of a circle. In one embodiment, the elongated body of the reconfigurable suture needle desirably has a semi-circular shape when in the first, high-profile configuration and a wave shape, such as a sine wave shape, when in the second, low-profile configuration.

In one embodiment, the joint may include a male/female connector that couples a distal end of the curved proximal section with a proximal end of the curved distal section. The joint enables the proximal and distal sections to be selectively rotated relative to one another for changing the profile, height and/or dimensions of the suture needle.

In one embodiment, the joint preferably includes a post projecting from one of the curved proximal and distal sections of the elongated body and a post opening formed in the other one of the curved proximal and distal sections of the elongated body. In one embodiment, the post projects distally from a distal end of the curved proximal section of the elongated body and the post opening is formed at the proximal end of the curved distal section of the elongated body.

In one embodiment, the joint may include a connector having a proximal face and a distal face, a first post extending proximally from the proximal face of the connector, and a second post extending distally from the distal face of the connector. In one embodiment, the curved proximal section of the elongated body has a distal end face with a first post opening that seats the first post, and the curved distal section of the elongated body has a proximal end face with a second post opening that seats the second post. The curved proximal and distal sections are preferably rotatable relative to one another via the joint for selectively changing the profile, height and/or dimensions of the suture needle.

In one embodiment, a method of passing a reconfigurable suture needle through a trocar preferably includes positioning the elongated body of the reconfigurable suture needle adjacent a trocar having an elongated conduit defining an inner diameter, rotating the curved proximal and distal sections of the elongated body into the second configuration having the lower profile so that the elongated body has a height that is less than or equal to the inner diameter of the elongated conduit of the trocar, and, after the rotating step, passing the elongated body through the elongated conduit of the trocar.

In one embodiment, the method preferably includes after passing the elongated body through the elongated conduit of the trocar, removing the elongated body from the trocar and again rotating the curved proximal and distal sections of the elongated body into the first configuration having the higher profile so that the elongated body has a height that is greater than the inner diameter of the elongated conduit of the trocar.

In one embodiment, the elongated body has a semi-circular shape when in the first configuration having the higher profile and a wave shape, such as a sine wave shape, when in the second configuration having the lower profile.

In one embodiment, a reconfigurable suture needle having sections rotatable about a joint desirably includes an elongated body having a curved proximal section and a curved distal section, and a joint interconnecting a distal end of the curved proximal section and a proximal end of the curved distal section for enabling the curved proximal and distal sections to rotate relative to one another between a first configuration having a higher profile and a second configuration having a lower profile.

In one embodiment, the elongated body desirably has a semi-circular shape when in the first configuration and a wave shape, such as a sine wave shape, when in the second configuration.

In one embodiment, the elongated body preferably has a greater height when in the first configuration and a smaller height when in the second configuration.

In one embodiment, the joint may include a male/female connector that couples a distal end of the curved proximal section with a proximal end of the curved distal section.

In one embodiment, the joint may include a post projecting distally from the distal end of the curved proximal section and a female opening formed in the proximal end of the curved distal section that receives the post for rotatably coupling the curved proximal section with the curved distal section.

In one embodiment, the joint preferably includes a connector having a proximal face and a distal face, a first post extending proximally from the proximal face of the connector, and a second post extending distally from the distal face of the connector. In one embodiment, the curved proximal section of the elongated body has a distal end face with a first female opening that seats the first post, and the curved distal section of the elongated body has a proximal end face with a second female opening that seats the second post.

In one embodiment, the curved proximal section of the elongated body preferably has a proximal end with a suture attachment hole.

In one embodiment, the curved distal section of the elongate body preferably has a distal end with a needle point.

In one embodiment, a suture needle may be reconfigured between a higher profile, semi-circular shape and a lower profile shape. The suture needle preferably includes an elongated body having at least two elongated, curved sections that may be connected together to form a semi-circular shaped body and disconnected from one another to form to form two smaller arc shaped sections that are tethered together by a suture thread. In one embodiment, a first curved section preferably has a sharp end (e.g., a needle point) and an opposing connecting end with a suture thread attached thereto. In one embodiment, a second curved section preferably includes a curved, hollow tube having a joining end. In one embodiment, the sections are configured to be connected to each other at a connecting end of the first section and the joining end of the second section, whereupon the suture thread passes through the curved, hollow tube of the second section and is secured to the connecting end of the first section of the elongated body. The two sections are small enough to be passable through a small trocar (e.g., a 5 mm trocar) when disconnected from one another, however, when the two sections are connected together to form a semi-circular shaped structure, the combined structure is too large to pass through the small trocar.

In one embodiment, a reconfigurable suture needle desirably includes an elongated body having a curved proximal section and a curved distal section. In one embodiment, the curved proximal section is preferably hollow and includes an elongated conduit extending from a proximal end to a distal end thereof. In one embodiment, the curved distal section preferably includes a needle point at a distal end thereof and a hollow post projecting proximally from a proximal end thereof.

In one embodiment, a suture thread passes through the elongated conduit of the curved proximal section. In one embodiment, the suture thread has a distal end that passes through the hollow post of the curved proximal section for being secured to the proximal end of the curved distal section.

In one embodiment, the elongated body preferably has a first configuration with a higher profile in which the hollow post of the curved distal section is inserted into the elongated conduit at the distal end of the curved proximal section.

In one embodiment, the elongated body has a second configuration with a lower profile in which the hollow post of the curved distal section is uncoupled from the elongated conduit at the distal end of the curved proximal section.

In one embodiment, the curved proximal section of the elongated body preferably defines about one-quarter (¼) of a circle and the curved distal section of the elongated body preferably defines about one-quarter (¼) of a circle.

In one embodiment, the elongated body desirably has a semi-circular shape when the curved proximal section and the curved distal section are connected together, whereby the elongated body is desirably in the first configuration having the higher profile.

In one embodiment, when the elongated body is in the second configuration with the lower profile, the curved proximal section and the curved distal section of the elongated body are desirably tethered together by the suture thread.

In one embodiment, the hollow post of the curved distal section has an outer diameter that preferably matches an inner diameter of the elongated conduit of the curved proximal section for forming a friction fit therebetween for holding the curved proximal and distal sections of the elongated body together.

In one embodiment, a suture needle having a joint preferably includes an elongated body having a curved proximal section with a suture attachment hole and a curved distal section with a sharpened tip. In one embodiment, the elongated body desirably has a joint located between the proximal and distal sections. In one embodiment, the joint enables the elongated body of the suture needle to be transformed from a first configuration having a greater dimension and a second configuration having a smaller dimension.

In one embodiment, the elongated body has a greater height when in the first configuration and a smaller height when in the second configuration.

In one embodiment, the elongated body has a semi-circular shape when in the first configuration and a wave shape when in the second configuration.

In one embodiment, when the elongated body has been rotated into the wave-shaped configuration (e.g., a sine wave) having the lower profile, the curved proximal section and the curved distal section of the elongated body may lie in a common plane.

In one embodiment, the curved proximal and distal sections of the elongated body may be made of medical grade or biocompatible stainless steel.

In one embodiment, the suture needle may be placed into a package in the rotated, lower-profile configuration so that the suture needle may be immediately ready to pass through the trocar upon being removed from the package. In one embodiment, after passing the suture needle in the low-profile configuration through a trocar to a surgical site, the needle may be rotated back into the high-profile configuration (e.g., a semi-circular configuration).

In one embodiment, a reconfigurable suture needle having a joint that allows for rotation may be marked (e.g., via laser marking) for easy identification, such as with a laser marking or a thermal marking.

In one embodiment, a larger sized suture needle may be provided (e.g., a CTX needle) that can still pass through a smaller trocar (e.g., a 5 mm trocar). Due to the presence of a joint on the elongated body of the suture needle, after the suture needle in the low-profile configuration has passed through the trocar, it may be reshaped to the high-profile configuration (e.g., a semi-circular configuration) by rotating the curved proximal and distal sections of the elongated body using laparoscopic instruments.

In the larger configuration (e.g., a semi-circular configuration), a surgeon may use the suture needle to perform a suturing operation. At the end of the suturing operation, the elongated body of the suture needle may be rotated back into the smaller shape (e.g., a wave shape, a sine wave shape) for extraction through the smaller diameter trocar (e.g., 5 mm trocar).

In one embodiment, the location of the joint along the length of the elongated body of the suture needle may be offset from a mid-point of the needle depending upon the size of the needle and the desired trocar size through which the needle will be passed.

Reshaping a suture needle having a rotating joint is much easier than reshaping a conventional suture needle having uniform high strength properties. Reshaping the needle in the surgical cavity is possible at low forces in a way that does not frustrate the surgeon and minimizes the potential for patient harm that can occur through needle sticks during reshaping high strength suture needles.

In one embodiment, the joint of the suture needle may be made of a first material and the curved proximal and distal sections of the suture needle may be made of a second material (e.g., stainless steel) that is different than the first material.

In one embodiment, premium alloys such as an ETHALLOY needle alloy, 4310 and the like may be used and combined with robust taper point designs (e.g. 6:1, or 8:1 tapers) to provide damage resistance. Stout taper ratios also desirably minimize the likelihood of needle points scraping the inside wall of the trocar. The suture needles having rotatable joints also desirably provide excellent damage resistance in robotic surgery and MIS surgery where extreme stresses can be applied to needles.

In one embodiment, during manufacturing and prior to being inserted into a package for shipment and storage, the suture needle may be rotated into a wave-shaped configuration so that it is first presented to a surgeon in the low-profile configuration. Providing a suture needle that is already rotated into the lower profile configuration when it is removed from the package preferably reduces the number of steps a surgeon must perform to pass the suture needle through a trocar and ensures that the right was shape is established out of the package to enable effective passage of suture needles through relatively smaller trocars (e.g., a 5 mm trocar).

In one embodiment, the wave-shaped needle may be passed through a trocar without substantial flex or friction because the rotated needle has outer dimensions that are smaller than the inner diameter of a 5 mm trocar. After the wave-shaped needle has been passed through the trocar for being delivered to the surgical site, gripping tools (e.g., needle drivers) may be used to rotate the suture needle to the higher profile configuration (e.g., a semi-circular shaped configuration, a half-circle shape) so that the needle may be used for surgery. After surgery, in order to remove the needle from the body, a surgeon may again rotate (e.g., with needle drivers) the curved proximal and distal sections of the suture needle back into the wave-shaped configuration so that the needle may be easily removed from the surgical cavity via the trocar.

In one embodiment, the rotatable joint may be in the middle of the suture needle or offset from the middle of the suture needle (e.g., somewhat closer to the point or barrel). In one embodiment, the rotatable joint may be located midway along the length of the suture needle between the distal tip and the proximal end of the needle.

In one embodiment, the space before the start of the tapered region of the suture needle provides a location for grasping the needle to pass the needle through a trocar or to change the shape of the needle. In one embodiment, locating the joint region closer to the distal needle point than the proximal end may result in the needle in the rotated configuration suffering less point damage as it passes through the trocar. In one embodiment, locating the joint closer to the distal tip than the proximal end of the elongated body may result in the suture needle being stronger in surgical use since the joint is nearer to the distal point and a somewhat lower bending moment at the joint location may occur.

In one embodiment, a suture needle may include an elongated body having at least two rotatable joints and at least three sections that are rotatable relative to one another about the joints for reconfiguring the elongated body of the suture needle from a high profile configuration to a low profile configuration. In one embodiment, a first joint interconnects first and second sections of an elongated body of a suture needle, and a second joint interconnects second and third sections of the elongated body of the suture needle. The first joint enables the first and second sections of the elongated body to rotate relative to one another, and the second joint enables the second and third sections of the elongated body to rotate relative to one another. One or more of the first, second and third sections of the elongated body may be curved or have an arc shape.

These and other preferred embodiments of the present patent application will be described in more detail below.

DETAILED DESCRIPTION OF PREFERRED EMBODIMENTS

Figures 1A, 1B:
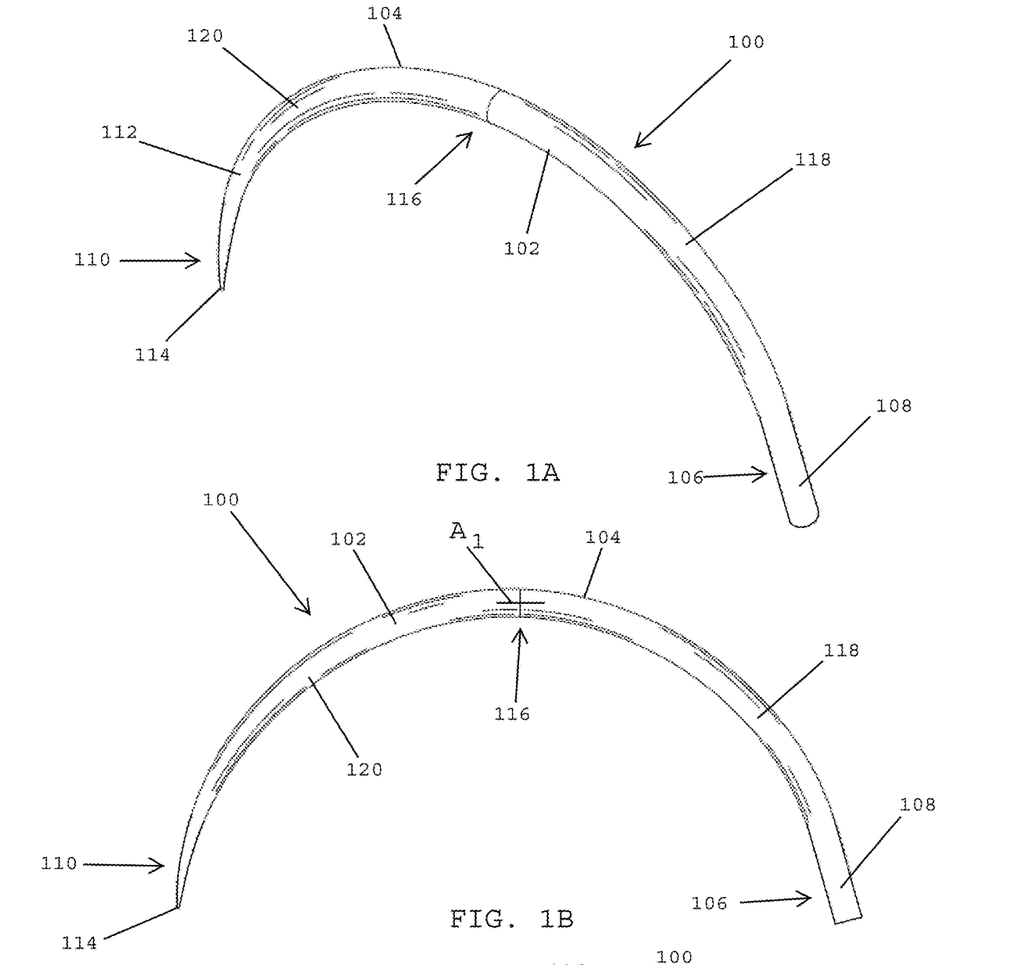
FIG. 1A shows a perspective view of a suture needle having a joint that enables proximal and distal sections of the suture needle to rotate relative to one another, in accordance with one embodiment of the present patent application.
FIG. 1B shows a side view of the suture needle shown in FIG. 1A.

Referring to FIGS. 1A and 1B, in one embodiment, a suture needle 100 preferably includes an elongated body 102 having an outer surface 104. In one embodiment, the elongated body 102 preferably includes a proximal end 106 with a suture mounting barrel 108 having a hole for receiving a suture thread (not shown) and a distal end 110 with a tapered region 112 having a sharpened needle point 114.

In one embodiment, the suture needle 100 preferably includes a joint 116 that divides the elongated body 102 of the suture needle into a proximal section 118 and a distal section 120. In one embodiment, the joint 116 enables the proximal and distal sections 118, 120 of the elongated body 102 to be rotated relative to one another for transforming the shape of the suture needle 100 from a higher profile (e.g., a semi-circular shape) for use as a suturing needle to a lower profile (e.g., a wave shape) for passing the suture needle through a trocar. In one embodiment, the joint 116 enables the suture needle 100 to be repeatedly transformed back and forth between the higher profile, semi-circular shaped configuration and the lower profile, wave-shaped configuration.

Figure 2:
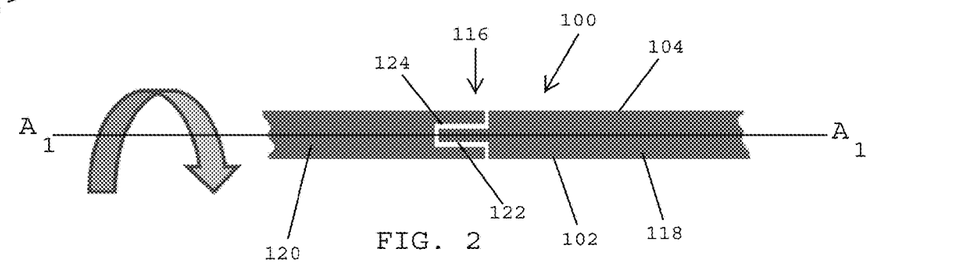
FIG. 2 shows a cross-sectional view of the joint of the suture needle shown in FIGS. 1A and 1B.

Referring to FIG. 2, in one embodiment, the joint 116 of the suture needle 100 preferably enables the opposing ends of the proximal and distal sections 118, 120 of the elongated body 102 of the suture needle 100 to be selectively rotated relative to one another about an axis designated $A_1$ (FIGS. 1B, 2). In one embodiment, the axis $A_1$ preferably passes through the joint 116 and the opposing ends of the proximal and distal sections 118, 120 of the elongated body 102 that are immediately adjacent to the joint 116. In one embodiment, the joint 116 may include a male projection 122 extending distally from the distal end of the first section 118 of the elongated body 102 and a female opening 124 located at a proximal end of the second section 120 of the elongated body 102. The male projection 122 of the proximal section 118 may be inserted into the female opening 124 of the distal section 120 for joining the proximal and distal sections 118, 120 together, which enables the two sections 118, 120 to be rotated relative to one another between higher profiles (e.g., a semi-circular shaped configuration) and lower profiles (e.g., a wave-shaped configuration).

Figure 3A:
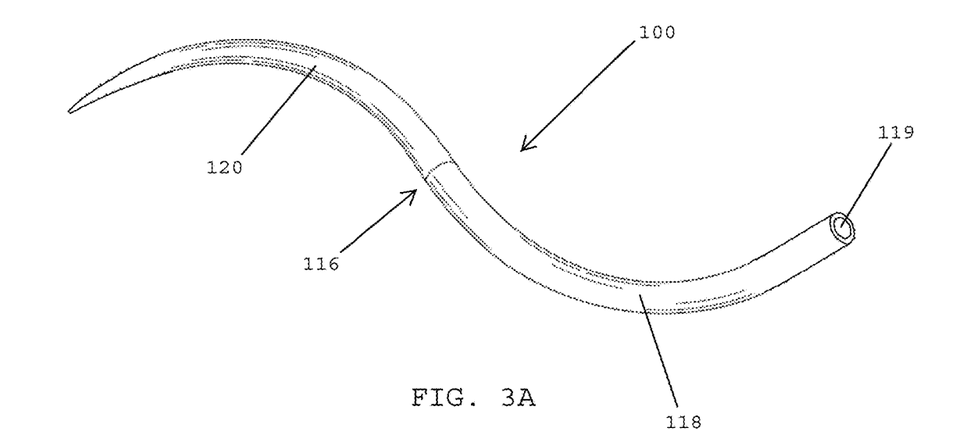
FIG. 3A shows a perspective view of the suture needle shown in FIGS. 1A and 1B after the proximal and distal sections of the suture needle have been rotated relative to one another, in accordance with one embodiment of the present patent application.
Figure 3B:
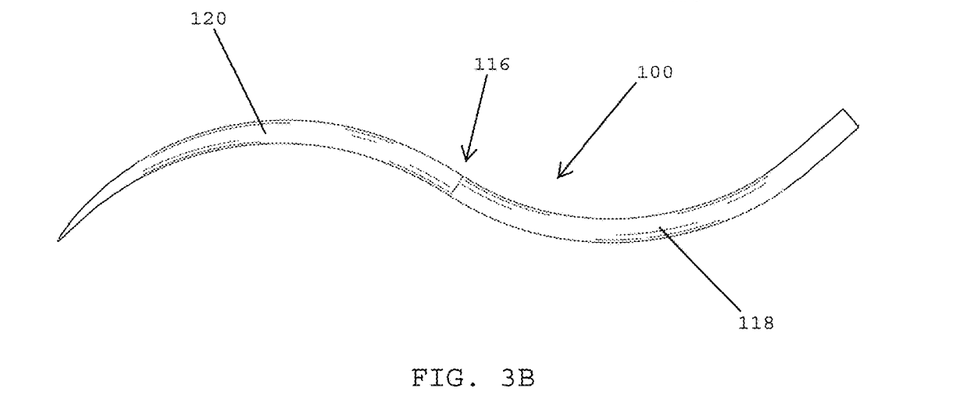
FIG. 3B shows a side view of the suture needle shown in FIG. 3A.

Referring to FIGS. 3A and 3B, in one embodiment, the joint 116 of the suture needle 100 enables the proximal and distal sections 118, 120 of the elongated body 102 to be rotated relative to one another from the higher profile, semi-circular shaped configuration shown in FIGS. 1A and 1B to the lower profile, wave-shaped configuration shown in FIGS. 3A and 3B. In one embodiment, the lower profile may have a wave shape (FIGS. 3A and 3B) and the higher profile may have a semi-circular shape (FIGS. 1A and 1B). In one embodiment, the proximal section 118 of the suture needle 100 preferably includes a suture attachment hole 119 (FIG. 3A) for attaching a suture thread to a proximal end of the suture needle 100.

Figure 3C:
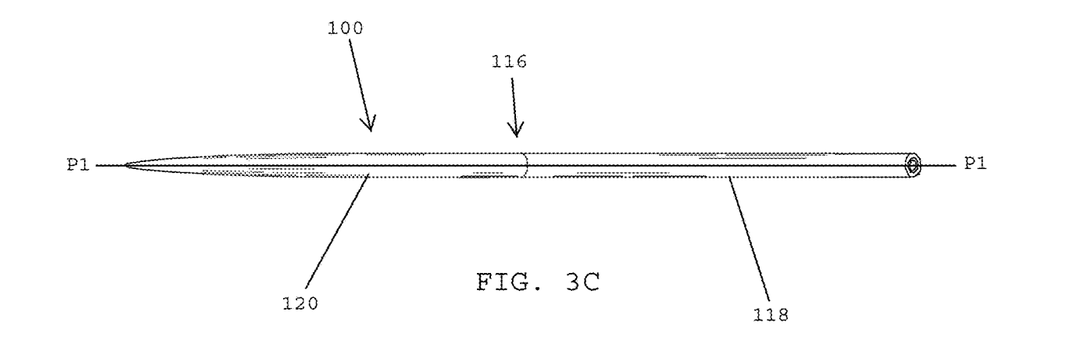
FIG. 3C shows a top plan view of the suture needle shown in FIGS. 3A and 3B.

In one embodiment, when the elongated body 102 has been rotated into the wave-shaped configuration of FIGS. 3A and 3B, the proximal section 118 of the elongated body 102 preferably defines a proximal arc, and the distal section 120 of the elongated body 102 preferably defines a distal arc. Referring to FIG. 3C, In one embodiment, when the elongated body 102 on the suture needle 100 is in the wave-shaped configuration, the proximal section 118, the distal section 120, and the joint 116 may lie in a common plane P1 (FIG. 2B).

Providing a suture needle with sections that are rotatable relative to one another preferably enables surgical personnel to reduce the overall height, profile and/or dimension of the suture needle so that it may be passed through smaller trocars, such as 5 mm trocars, that are typically used in minimally invasive surgeries (MIS) and/or robotic surgeries.

Figure 4:
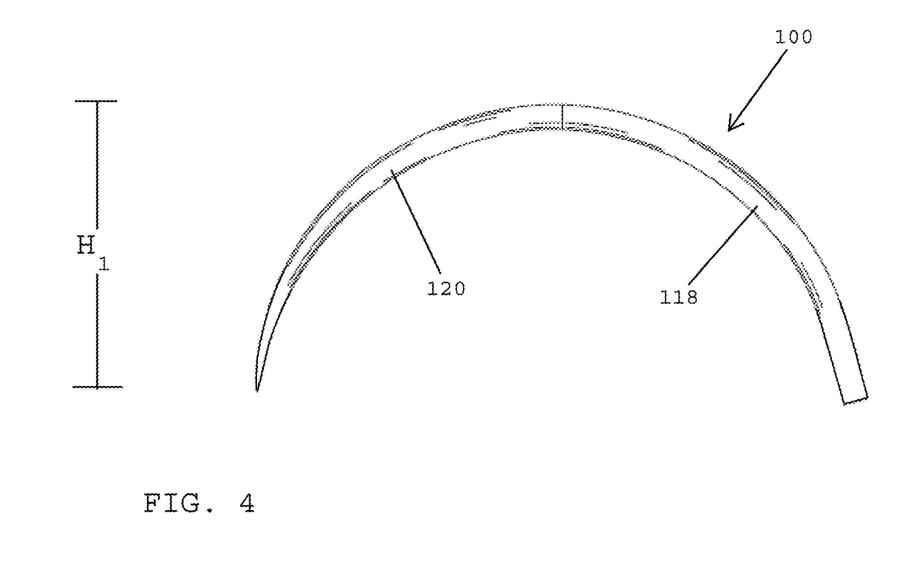
FIG. 4 shows a side view of a suture needle having a joint that enables proximal and distal sections of the suture needle to rotate relative to one another, the suture needle being in a semi-circular shaped configuration, in accordance with one embodiment of the present patent application.
Figure 5:
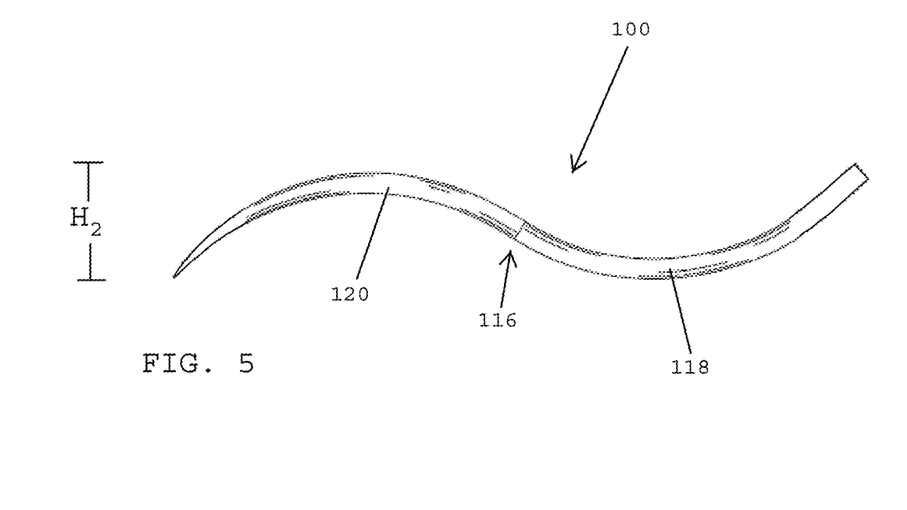
FIG. 5 shows a side view of the suture needle of FIG. 4 with the suture needle rotated into a wave-shaped configuration, in accordance with one embodiment of the present patent application.

A comparison of the height, profile and/or dimension change that may be made to the suture needle 100 (FIGS. 1A-1B and 3A-3C) having rotatable proximal and distal sections 118, 120 may be seen in FIGS. 4 and 5. Referring to FIG. 4, in one embodiment, prior to being rotated from a higher profile, semi-circular shaped configuration to a lower profile, wave-shaped configuration, the suture needle 100 desirably has a height $H_1$ of greater than 5 mm, more preferably about 10-15 mm, and even more preferably about 13 mm. Referring to FIG. 5, in one embodiment, after the suture needle 100 has been rotated about the joint 116 into the lower profile, wave-shaped configuration, the suture needle 100 desirably has a height $H_2$ of about 5 mm or less, which is less than the height $H_1$ of the suture needle 100 in the higher profile configuration shown in FIG. 4. Thus, when the suture needle 100 has the higher profile shown in FIG. 4, the suture needle may not pass through a smaller trocar (e.g., 5 mm trocar), however, when the suture needle 100 has the lower profile shown in FIG. 5, the suture needle may be readily passed through the smaller trocar.

Figure 6A:
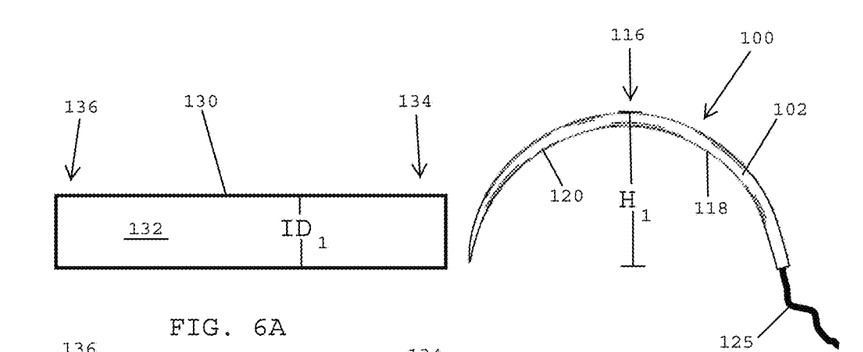
FIG. 6A shows a first stage of a method of passing a suture needle through a trocar, in accordance with one embodiment of the present patent application.

Referring to FIG. 6A, in one embodiment, the suture needle 100 includes the joint 116 that enables the proximal section 118 and the distal section 120 on the elongated body 102 to be rotated relative to one another. In FIG. 6A, the proximal and distal sections 118, 120 are rotated about the joint 116 so that the elongated body has a semi-circular shaped configuration having a relatively higher profile height $H_1$ of greater than 5 mm, more preferably about 10-15 mm, and even more preferably about 13 mm. The suture needle 100 desirably has a suture thread 125 secured (e.g., swage, crimped) to the barrel 108 at the proximal end 106 thereof. The suture needle 100 may be juxtaposed with a trocar 130 so that the needle point 114 on the distal section 120 of the suture needle 100 defines the leading end of the suture needle 100. The trocar 130 (e.g., a 5 mm trocar) may have an elongated conduit 132 that extends from a first opening at a proximal end 134 of the trocar to a second opening at a distal end 136 of the trocar. The elongated conduit 132 of the trocar 130 preferably has an inner diameter $ID_1$ that is less than the height $H_1$ of the elongated body 102 of the semi-circular shaped suture needle 100. As a result, the semi-circular shaped suture needle 100 has a profile and/or height that is too large to pass through the elongated conduit 132 of the trocar 130.

Figure 6B:
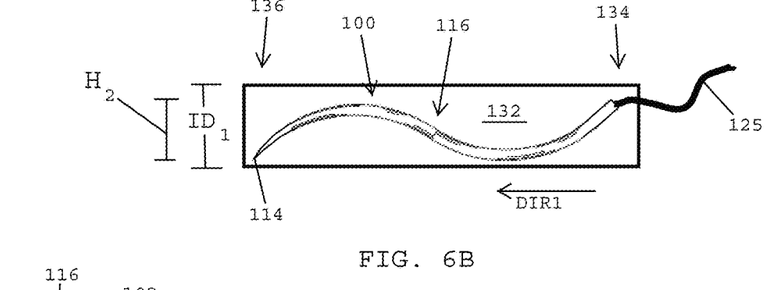
FIG. 6B shows a second stage of a method of passing a suture needle through a trocar, in accordance with one embodiment of the present patent application.

Referring to FIG. 6B, in one embodiment, the suture needle 100 shown in FIG. 6A may be rotated at the joint 116 into a wave-shaped configuration having a lower profile and/or height so that the elongated body 102 of the suture needle 100 now has a height $H_2$ (e.g., 5 mm), which is less than the height $H_1$ of the suture needle in the semi-circular shaped configuration (FIG. 6A) and less than the height of the inner diameter $ID_1$ of the elongated conduit 132 of the trocar 130. As a result, in the lower profile, wave-shaped configuration of FIG. 6B, the suture needle 100 may readily pass through a first opening at the proximal end 134 of the trocar 130, be advanced distally in the direction DIR1 through the elongated conduit 132, and be removed from a second opening at the distal end 136 of the trocar, for being positioned at a surgical site inside a patient. In one embodiment, the needle point 114 of the distal section 120 of the suture needle 100 is preferably the leading end of the suture needle as the suture needle is passed through the trocar, and the proximal section 118 of the suture needle and the attached suture thread 125 trails the distal section 120. In one embodiment, the tapered distal end 112 of the suture needle 100 may be grasped by a needle driver for passing the suture needle through the elongated conduit 132 of the trocar 130. The jaws of the needle driver may surround and protect the needle point 114 as the suture needle is passed through the trocar. In one embodiment, the proximal section of the suture needle may be the leading end of the suture needle as it is passed through a trocar, with the distal end of the suture needle trailing the proximal end.

Figure 6C:
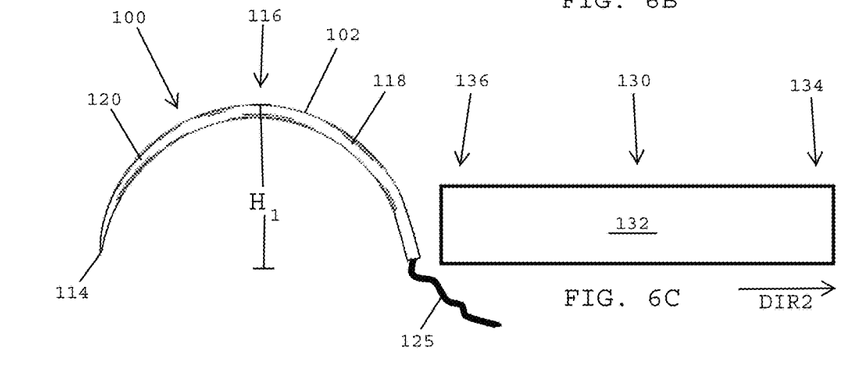
FIG. 6C shows a third stage of a method of passing a suture needle through a trocar, in accordance with one embodiment of the present patent application.

Referring to FIG. 6C, in one embodiment, after the wave-shaped suture needle 100 shown in FIG. 6B has been removed from the second opening at the distal end 136 of the trocar 130, a surgeon may transform and/or reshape the suture needle 100 from the wave-shaped configuration (FIG. 6B) back to the original, semi-circular shaped configuration having the height $H_1$ (FIG. 6A). The suture needle 100 in the higher profile, semi-circular shaped configuration may be utilized for suturing tissue. At that end of a suturing operation, a surgeon may once again rotate the proximal and distal sections 118, 120 of the elongated body 102 about the joint 116 of the suture needle 100 so that the suture needle is returned to the lower profile, wave-shaped configuration (FIG. 6B) for being withdrawn in the direction DIR2 through the elongated conduit 132 of the smaller diameter trocar 130. In one embodiment, the needle driver may clamp onto the needle point 114 of the suture needle, the elongated body 102 of the suture needle, the suture attachment barrel 108, or the suture thread 125 attached to the proximal end of the elongated body of the suture needle for extracting and/or pulling the suture needle through the trocar 130 to remove the suture needle from the surgical cavity.

Figure 7:
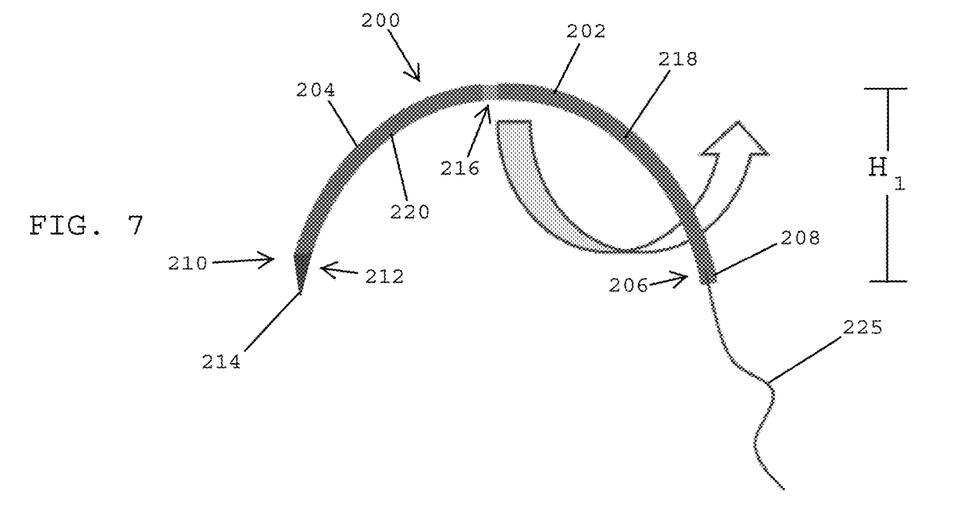
FIG. 7 shows a side view of a suture needle having a joint that enables proximal and distal sections of the suture needle to rotate relative to one another, in accordance with one embodiment of the present patent application.

Referring to FIG. 7, in one embodiment, a suture needle 200 having proximal and distal sections 218, 220 that are rotatable relative to one another about a joint 216 for changing the height, profile and/or configuration of the suture needle 200 preferably includes an elongated body 202 having an outer surface 204. In one embodiment, the elongated body 202 extends from a proximal end 206 having a suture attachment barrel 208 that defines a proximal-most end of the suture needle to a distal end 210 having a tapered region 212 with a sharpened needle point 214 that defines a distal-most end of the suture needle 200. In one embodiment, the suture needle 200 preferably includes the joint 216 that divides the elongated body 202 into the proximal section 218 and the distal section 220. Each of the proximal and distal sections 218, 220 may have respective arc shapes. In one embodiment, the joint 216 is preferably located approximately midway along the length of the elongated body 202 of the suture needle 200 between the proximal end 208 and the distal end 210 of the elongated body 202. A suture thread 225 may be secured to the barrel 208 of the elongated body 202 of the suture needle 200.

Figure 8:
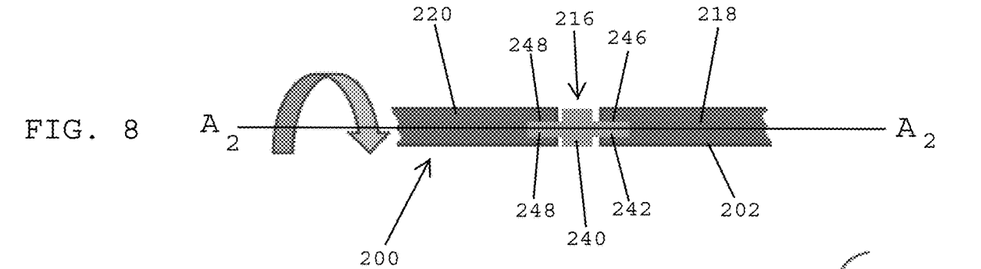
FIG. 8 shows a cross-sectional view of the joint of the suture needle shown in FIG. 7.

Referring to FIGS. 7 and 8, in one embodiment, the joint 216 of the suture needle 200 is preferably located between a distal end of the proximal section 218 of the elongated body 202 and a proximal end of the distal section 220 of the elongated body 202 for enabling the proximal and distal sections 218, 220 of the elongated body 202 to rotate relative to one another. Referring to FIG. 8, in one embodiment, the joint 216 may include a connector 240 having a first post 242 that extends proximally from the connector 240 and a second post 244 that extends distally from the connector 240. The distal end of the proximal section 218 desirably includes a first female opening 246 that receives the first post 242 of the joint 216 and the proximal end of the distal section 220 preferably includes a second female opening 248 that receives the second post 244 of the joint 216. The joint 216 preferably holds the proximal and distal sections 218, 220 of the elongated body 202 together while enabling the proximal and distal sections to rotate relative to one another for changing the height, profile and/or shape of the suture needle 200.

Referring to FIG. 8, in one embodiment, the joint 216 of the suture needle 200 preferably enables the opposing ends of the proximal and distal sections 218, 220 of the elongated body 202 of the suture needle 200 to be selectively rotated relative to one another about an axis designated $A_2$. In one embodiment, the axis $A_2$ preferably passes through the connector 240 and the first and second posts 242, 244 of the joint 216, as well as the opposing ends of the proximal and distal sections 218, 220 of the elongated body 202 that are immediately adjacent to the joint 216.

Figure 9:
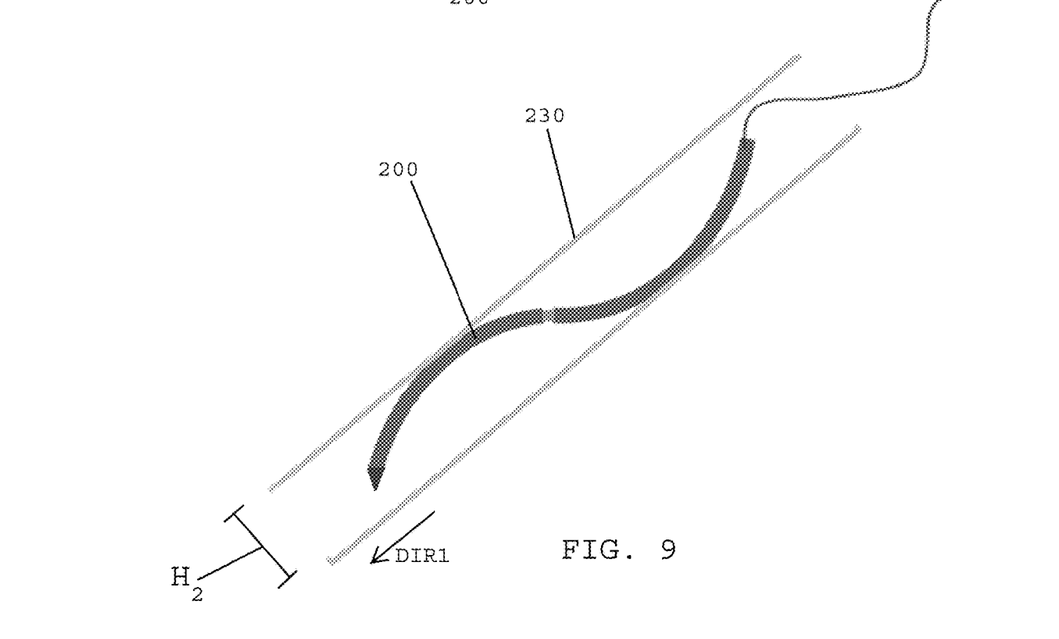
FIG. 9 shows a method of passing the suture needle of FIGS. 7 and 8 through a trocar, in accordance with one embodiment of the present patent application.

In one embodiment, the suture needle 200 shown and described above in FIGS. 7 and 8 may be transformed from a higher profile (e.g., a semi-circular shaped configuration) to a lower profile (e.g., a wave shaped configuration). Referring to FIG. 9, in one embodiment, the proximal and distal sections 218, 220 of the elongated body 202 of the suture needle 200 may be rotated about the joint 216 to reconfigure the suture needle into a wave-shaped configuration. In the wave-shaped configuration of FIG. 9, the suture needle 200 preferably has a lower profile and/or smaller height $H_2$ than when the suture needle 200 is in the semi-circular configuration having a height $H_1$ (FIG. 7) that is greater than the smaller height $H_2$. The proximal and distal sections 218, 220 of the suture needle 200 preferably maintain their respective arc shapes in both the semi-circular shaped configuration (FIG. 7) and the wave-shaped configuration (FIG. 9). In the wave-shaped configuration, the suture needle has a lower profile, which reduces the height of the needle so that it may be passed through a smaller trocar 230 (e.g., a 5 mm trocar) in the distal direction DIR1 (FIG. 9).

Figure 10:
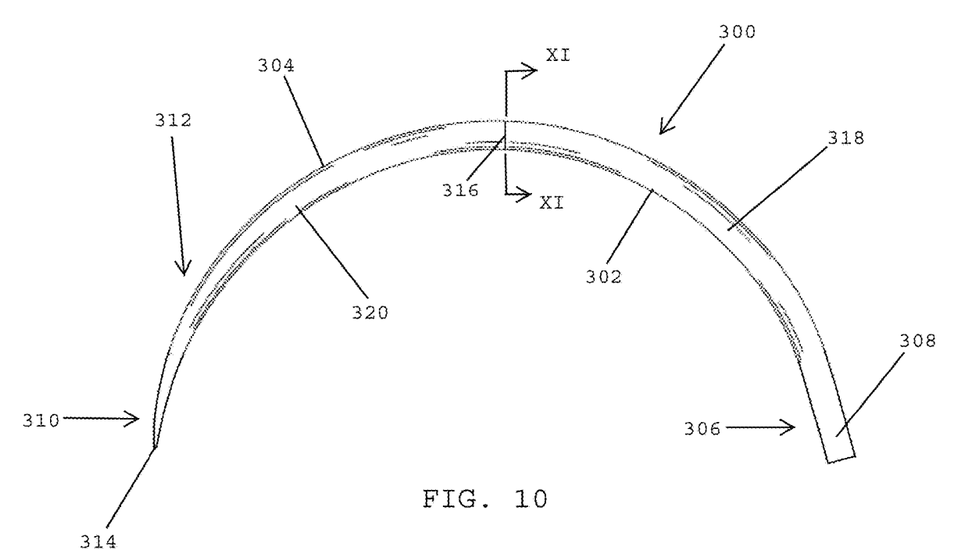
FIG. 10 shows a side view of a suture needle having a joint that enables proximal and distal sections of the suture needle to rotate relative to one another, in accordance with one embodiment of the present patent application.

Referring to FIG. 10, in one embodiment, a suture needle 300 preferably includes an elongated body 302 having an outer surface 304. In one embodiment, the elongated body 302 preferably includes a proximal end 306 with a suture mounting barrel 308 having a hole for receiving a suture (not shown) and a distal end 310 with a tapered region 312 having a sharpened needle point 314.

In one embodiment, the suture needle 300 preferably includes a joint 316 that divides the elongated body 302 of the suture needle into a proximal section 318 and a distal section 320. In one embodiment, the proximal and distal sections 318, 320 have respective arc shapes. In one embodiment, the joint 116 couples the proximal and distal sections 318, 320 together and preferably enables the proximal and distal sections 118, 120 to rotate relative to one another for transforming the shape of the suture needle 100 from a semi-circular shapes configuration (FIG. 10) having a higher profile to a wave-shaped configuration (FIG. 12) having a lower profile for passing the suture needle 300 through a small trocar (e.g., a 5 mm trocar).

Figure 11:
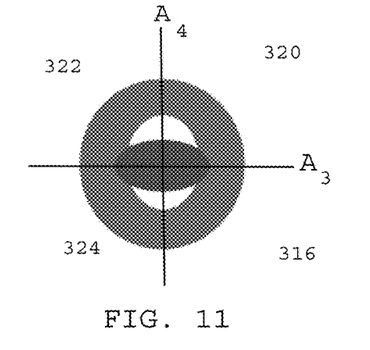
FIG. 11 shows a cross-sectional view of the suture needle of FIG. 10 taken along line XI-XI of FIG. 10.
Figure 12:
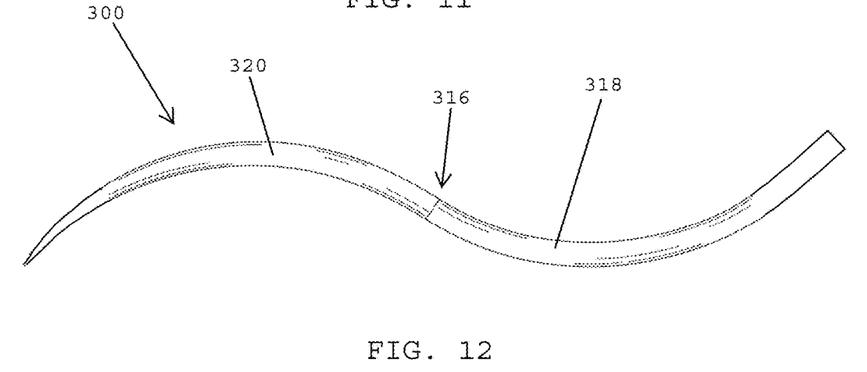
FIG. 12 shows a side view of the suture needle shown in FIGS. 10 and 11 after the suture needle has been rotated into a wave-shaped configuration, in accordance with one embodiment of the present patent application.

Referring to FIGS. 11 and 12, in one embodiment, the joint 316 may include a male post 322 that projects distally from the distal end of the proximal section 318 of the elongated body 302 and a female opening 324 formed at the proximal end of the distal section 320 of the elongated body 302. In one embodiment, the male post 322 preferably has an oval-shaped cross-section having a longitudinal axis $A_3$, and the female opening 324 desirably has an oval-shaped cross-section having a longitudinal axis $A_4$. The male post 322 may be inserted into the female opening 324 for joining the proximal and distal sections together. The free end of the male post 322 may be swaged for maintaining a rotatable connection between the proximal and distal sections 318, 320 of the elongated body 302 of the suture needle 300.

In one embodiment, the proximal and distal sections 318, 320 of the suture needle 300 may be rotated relative to one another to place the sections into the semi-circular shaped configuration shown in FIG. 10. In the semi-circular shaped configuration, the longitudinal axis $A_3$ of the oval-shaped cross section of the male post 322 is generally perpendicular to the longitudinal axis $A_4$ of the oval-shaped cross section of the female opening 324, which preferably generates a friction lock formed between the proximal and distal sections 318, 320 of the suture needle 300 for holding the suture needle in the semi-circular shaped configuration.

Referring to FIGS. 11 and 12, in one embodiment, the proximal and distal sections 318, 320 of the suture needle 300 may be rotated relative to one another about the joint 316 so that the longitudinal axis $A_3$ of the oval-shaped cross section of the male post 322 is generally parallel to the longitudinal axis $A_4$ of the oval-shaped cross section of the female opening 324, which eliminates the friction lock and positions the proximal and distal sections 318, 320 of the elongated body 302 of the suture needle 300 into the wave-shaped configuration shown in FIG. 12.

Figure 13A:
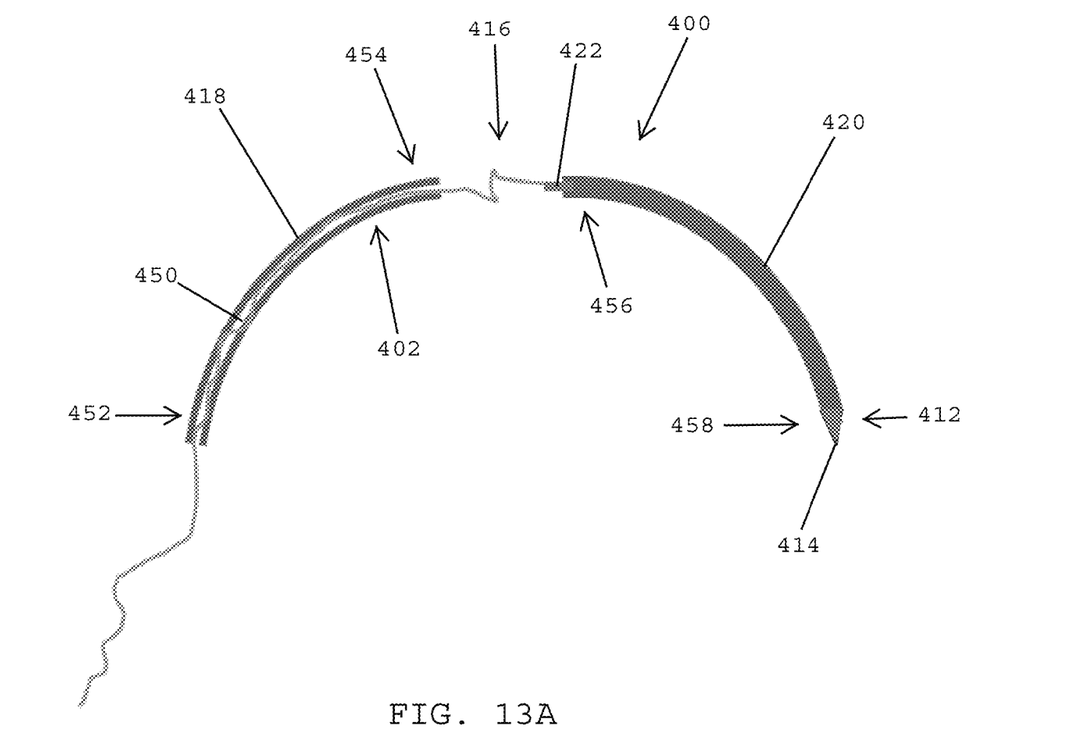
FIG. 13A shows a side view of a suture needle having a joint that enables proximal and distal sections of the suture needle to be uncoupled from one another, in accordance with one embodiment of the present patent application.
Figure 13B:
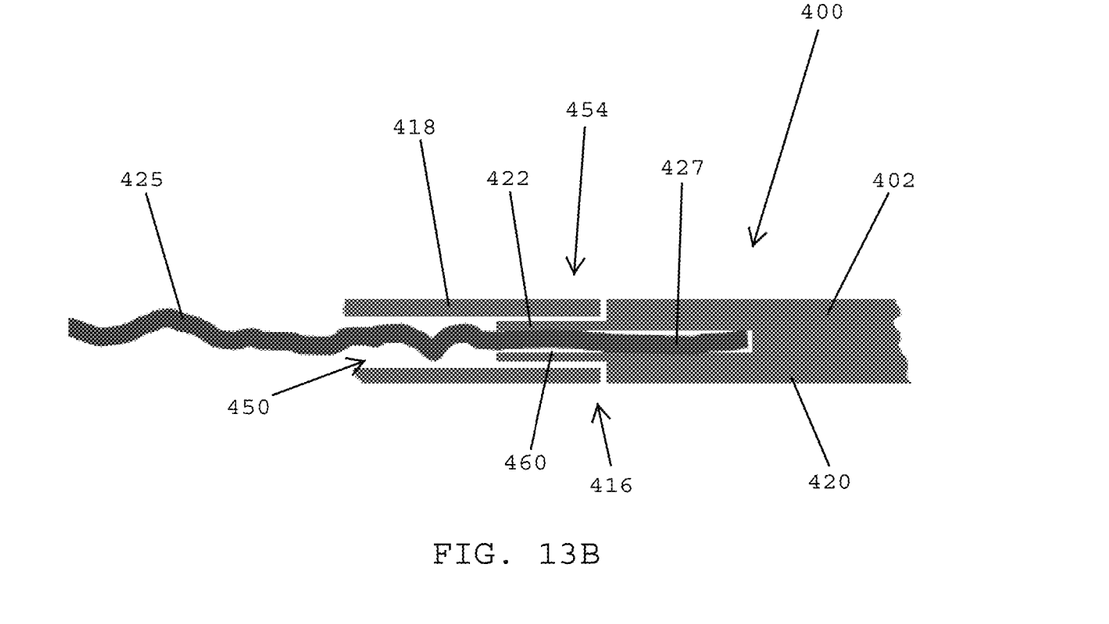
FIG. 13B shows a cross-sectional view of the joint shown in FIG. 13A.

Referring to FIGS. 13A and 13B, in one embodiment, a suture needle 400 preferably includes an elongated body 402 having a joint 416 located between a proximal section 418 and a distal section 420 of the elongated body. In one embodiment, the joint 416 desirably enables the proximal and distal sections 418, 420 on the elongated body 402 to be uncoupled from one another for lowering the profile of the suture needle 400 so that it may be passed through a trocar. In one embodiment, after the suture needle 400 has been passed through a trocar, the joint 416 enables the proximal and distal sections 418, 420 of the elongated body 402 to be re-coupled together to form a higher profile structure (e.g., a semi-circular shaped suture needle) for use as a suturing needle.

In one embodiment, the proximal section 418 of the suture needle 400 preferably defines a curved, hollow tube having an elongated conduit 450 that extends from a proximal end 452 to a distal end 454 thereof.

In one embodiment, the distal section 420 of the suture needle 400 preferably has a proximal end 456 and a distal end 458. In one embodiment, the distal end 458 of the distal section 420 of the suture needle preferably includes a tapered distal end 412 that terminates at a needle point 414, which preferably defines a distal-most end of the suture needle 400. In one embodiment, the proximal end 456 of the distal section 420 preferably includes a male post 422 that projects from the proximal end 456. The male post 422 preferably defines an elongated conduit 460 (FIG. 13B) that is adapted to receive a distal end 427 of a suture thread 425. After passing through the elongated conduit 460, a distal end 427 of the suture thread 425 may be secured to the proximal end 456 of the distal section 420 of the suture needle 400, such as by swaging or crimping the proximal end 456 of the distal section 420 of the elongated body 402 of the suture needle 400.

Referring to FIG. 13B, in one embodiment, the distal-most end 427 of the suture thread is preferably secured to the proximal end 456 of the distal section 420 of the suture needle 400. The suture thread 425 preferably passes through the elongated conduit 460 of the male post 422 and the hollow tube of the proximal section 418 of the suture needle 400 for extending out of an opening at the proximal end 452 of the hollow tube of the proximal section 418. The male post 422 may be inserted into the opening at the distal end 454 of the proximal section 418 for forming a friction fit between the proximal and distal sections 418, 420 of the suture needle 400. In one embodiment, the outer diameter of the male post 422 preferably closely matches the inner diameter of the elongated conduit 450 of the hollow tube of the proximal section 418 of the elongated body 402 of the suture needle 400, which enables the formation of a friction fit between the proximal and distal sections 418, 420 of the elongated body 402 of the suture needle 400. In one embodiment, the preferably enables the proximal and distal sections 418, 420 of the suture needle 400 to rotate relative to one another for transforming the suture needle from a higher profile, semi-circular shaped configuration (e.g., FIG. 1A) to a lower profile, wave-shaped configuration (e.g., FIG. 3A).

Figure 14:
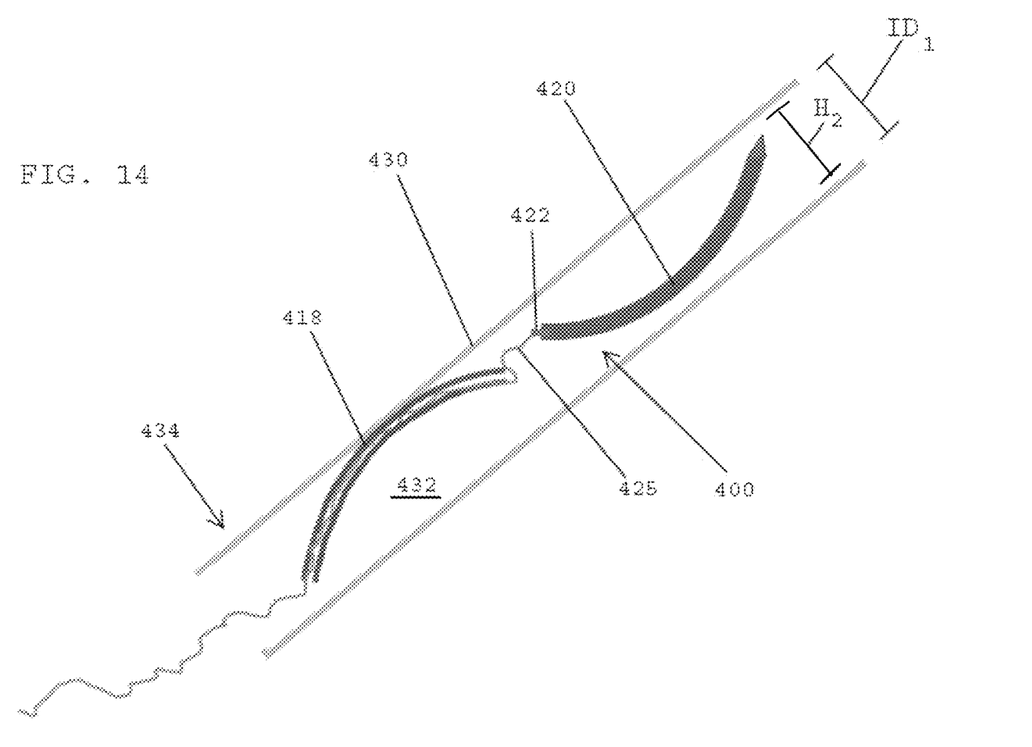
FIG. 14 shows a method of passing the suture needle of FIGS. 13A and 13B through a trocar, in accordance with one embodiment of the present patent application.

Referring to FIG. 14, in one embodiment, the male post 422 of the distal section 420 may be uncoupled from the female opening at the distal end 454 of the proximal section 418 so that the proximal and distal sections 418, 420 are detached from one another. The proximal and distal sections 418, 420 remain tethered to one another via the suture thread 425 that has a distal-most end secured to the proximal end 456 of the distal section 420 and a proximal section that passes through the curved hollow tube of the proximal section 418.

When the proximal and distal sections 418, 420 are uncoupled, each of the individual sections define a respective arc-shaped structure having a height $H_2$ that is less than the inner diameter $ID_1$ of the conduit 432 of the trocar 430. In one embodiment, the uncoupled proximal and distal sections 418, 420 of the suture needle may be passed through the elongated conduit 432 of the trocar 430 for being positioned at a surgical site.

Figure 15:
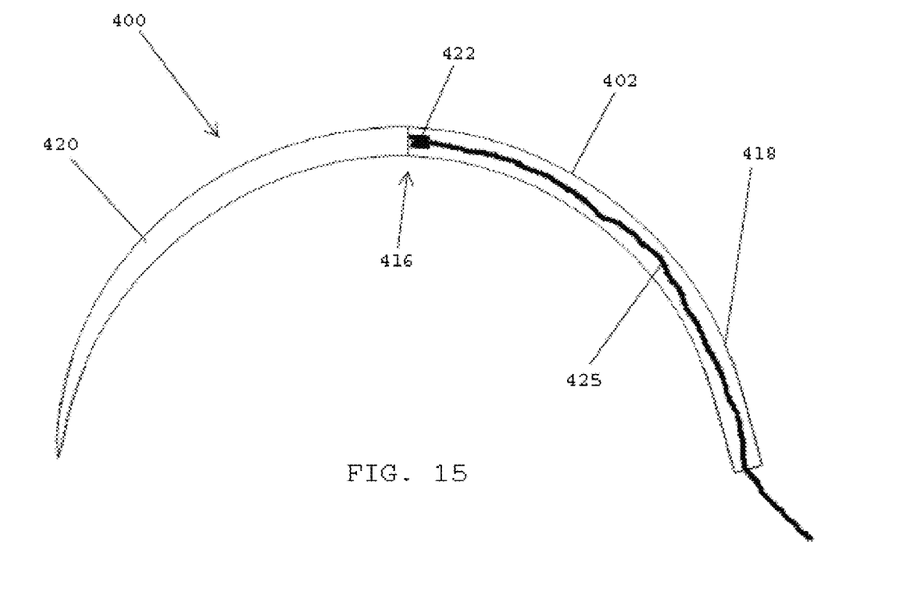
FIG. 15 shows the suture needle of FIGS. 13A and 13B with the proximal and distal sections of the suture needle joined together via a joint, in accordance with one embodiment of the present patent application.

Referring to FIG. 15, in one embodiment, after the uncoupled proximal and distal sections 418, 420 of the elongated body 402 of the suture needle 400 have been delivered through the trocar to a surgical site, the proximal and distal sections 418, 420 may be joined together via the joint 416 for providing a suture needle 400 having a higher profile, semi-circular shaped configuration. In one embodiment, the distal end of a suture thread 425 is secured to the male post 422 located at the proximal end of the distal section 420. The suture thread 425 preferably passes through the hollow channel of the proximal section 418. At the end of a surgical procedure, the proximal and distal sections 418, 420 may be uncoupled from one another (e.g., as shown in FIG. 14) for removing the suture needle from the surgical site and withdrawing the suture needle from the proximal end 434 of the trocar 430 (FIG. 14).

Providing a suture needle with proximal and distal sections that are rotatable or reconfigurable relative to one another preferably enables surgical personnel to selectively reduce the overall height, profile and/or dimension of the suture needle so that it may be passed through smaller trocars (e.g., 5 mm trocars) that are typically used in minimally invasive surgeries (MIS) and/or robotic surgeries.

In the lower profile configuration disclosed herein, the suture needle may be passed through a trocar to a surgical site. Once the suture needle has reached the surgical site, a surgeon may transform the suture needle to a higher profile, semi-circular shaped configuration for use during a suturing procedure. Once the suturing procedure has been completed at the surgical site, a surgeon may once again transform the suture needle back to the lower profile configuration (e.g., the wave-shaped configuration) for reducing the profile of the needle to remove the suture needle from the surgical site via a trocar.

In one embodiment, the suture needles disclosed herein may incorporate one or more of the features and/or embodiments disclosed in commonly assigned U.S. patent application Ser. No. 16/282,604, filed Feb. 22, 2019, the disclosure of which is hereby incorporated by reference herein. In one embodiment, the above-reference '604 patent application discloses a suture needle including an elongated body having a proximal section, a distal section, and a bendable region located between the proximal and distal sections. The bendable region has a reduced cross-section and/or is made of a superelastic material that is more flexible than the proximal and distal sections of the elongated body for enabling the suture needle to transform from a first configuration having a larger dimension to a second configuration having a smaller dimension. When in the first configuration, the suture needle is larger than an inner diameter of an elongated conduit of a trocar. In order to pass the suture needle through the elongated conduit of the trocar, the elongated body is bent at the bendable region so that the suture needle is smaller than the inner diameter of the elongated conduit of the trocar. After passing the suture needle through the trocar, the elongated body is bent back to the first, larger dimension to configure the suture needle for use for suturing tissue.

In one embodiment, the suture needles disclosed herein may incorporate one or more of the features and/or embodiments disclosed in commonly assigned U.S. patent application Ser. No. 16/282,652, filed Feb. 22, 2019, the disclosure of which is hereby incorporated by reference herein. In one embodiment, the '652 patent application discloses a method of making a suture needle having a bendable region. The method includes obtaining a suture needle made of a martensitic alloy having an austenitic transition temperature. In one embodiment, the suture needle has a proximal section, a distal section with a sharpened tip, and a bendable region located between the proximal and distal sections. The method includes heating the suture needle to a first temperature that is greater than the austenitic transition temperature of the martensitic alloy and quenching the suture needle to room temperature to harden the martensitic alloy. After heating and quenching, the bendable region of the suture needle is heated locally to a second temperature that is above 800 degrees Celsius, but below the austenitic transition temperature of the martensitic alloy so that the bendable region is softened and made more flexible relative to the proximal and distal sections of the suture needle. The local heating of the bendable region is by electrical resistance heating, laser heating, induction heating, flame heating, or hot gas heating. The suture needle is preferably tempered to improve ductility.

In one embodiment, the suture needles disclosed herein may incorporate one or more of the features and/or embodiments disclosed in commonly assigned U.S. Provisional Application Ser. No. 62/809,016, filed Feb. 22, 2019, the disclosure of which is hereby incorporated by reference herein. In one embodiment, the '016 provisional application discloses an elastic suture needle that may be passed through a smaller trocar for use in minimally invasive surgery. In one embodiment, the suture needle preferably includes an elongated body having a proximal end, a distal end, a length extending from the proximal end to the distal end, a top surface extending along the length of the elongated body, and a bottom surface extending along the length of the elongated body. The elongated body has dimensions that are calculated using the equation $T/L_N < (4*\sigma)/(\pi E)$, where T is the thickness of the elongated body, $L_N$ is the length of the elongated body, $\sigma$ is the yield strength of the elongated body, and E is the Young's modulus of the elongated body. The elongated body is preferably made of stainless steels such as martensitic stainless steels, austenitic stainless steels, martensitic-aged (mar-aged) stainless steels, and stainless steels sold under the registered trademark ETHALLOY®.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A reconfigurable suture needle comprising:
   an elongated body having a curved proximal section with a suture attachment end and a curved distal section with a tissue penetrating end;
   a joint interconnecting a distal end of said curved proximal section and a proximal end of said curved distal section, wherein said joint enables said curved proximal section and said curved distal section to rotate relative to one another about an axis that passes through said joint and opposing ends of said curved proximal and distal sections that are immediately adjacent to said joint for transforming said elongated body between a first configuration having a higher profile and a second configuration having a lower profile.

2. The reconfigurable suture needle as claimed in claim 1, wherein said elongated body of said suture needle has a greater height when in the first configuration and a smaller height when in the second configuration.

3. The reconfigurable suture needle as claimed in claim 2, wherein each of said curved proximal and distal sections of said elongated body defines about one-quarter (¼) of a circle.

4. The reconfigurable suture needle as claimed in claim 3, wherein said elongated body of said reconfigurable suture needle has a semi-circular shape when in the first configuration and a sine wave shape when in the second configuration.

5. The reconfigurable suture needle as claimed in claim 1, wherein said joint comprises a male/female connector that couples the distal end of said curved proximal section with the proximal end of said curved distal section.

6. The reconfigurable suture needle as claimed in claim 5, wherein said joint comprises a post projecting from one of said curved proximal and distal sections and a post opening formed in the other one of said curved proximal and distal sections.

7. The reconfigurable suture needle as claimed in claim 5, wherein said joint comprises:
   a connector having a proximal face and a distal face;
   a first post extending proximally from the proximal face of said connector;
   a second post extending distally from the distal face of said connector;
   said curved proximal section of said elongated body having a distal end face with a first post opening that seats said first post;
   said curved distal section of said elongated body having a proximal end face with a second post opening that seats said second post;
   wherein said curved proximal and distal sections are rotatable relative to one another via said joint.

8. A method of passing said reconfigurable suture needle of claim 1 through a cannula comprising:
   positioning said elongated body of said reconfigurable suture needle adjacent said cannula having an elongated conduit defining an inner diameter;
   rotating said curved proximal and distal sections of said elongated body into the second configuration having the lower profile so that said elongated body has a height that is less than or equal to the inner diameter of said elongated conduit of said cannula;
   after the rotating step, passing said elongated body through said elongated conduit of said cannula;
   after passing said elongated body through said elongated conduit of said cannula, removing said elongated body from said cannula and again rotating said curved proximal and distal sections of said elongated body into the first configuration having the higher profile so that said elongated body has a height that is greater than the inner diameter of said elongated conduit of said cannula.

9. The method as claimed in claim 8, wherein said elongated body has a semi-circular shape in the first configuration having the higher profile and a sine wave shape in the second configuration having the lower profile.

10. A reconfigurable suture needle having sections rotatable about a joint comprising:
    an elongated body having a curved proximal section and a curved distal section;
    said joint interconnecting a distal end of said curved proximal section and a proximal end of said curved distal section for enabling said curved proximal and distal sections to rotate relative to one another between a first configuration having a higher profile and a second configuration having a lower profile;
    wherein said elongated body has a semi-circular shape when in the first configuration and a wave shape when in the second configuration.

11. The reconfigurable suture needle as claimed in claim 10, wherein the wave shape of said elongated body when in the second configuration comprises a sine wave shape.

12. The reconfigurable suture needle as claimed in claim 10, wherein said elongated body has a greater height when in the first configuration and a smaller height when in the second configuration.

13. The reconfigurable suture needle as claimed in claim 10, wherein said joint comprises a male/female connector that couples a distal end of said curved proximal section with a proximal end of said curved distal section.

14. The reconfigurable suture needle as claimed in claim 13, wherein said joint comprises a post projecting distally from the distal end of said curved proximal section and a female opening formed in the proximal end of said curved distal section that receives said post for rotatably coupling said curved proximal section with said curved distal section.

15. The reconfigurable suture needle as claimed in claim 13, wherein said joint comprises:
    a connector having a proximal face and a distal face;
    a first post extending proximally from the proximal face of said connector;
    a second post extending distally from the distal face of said connector;
    said curved proximal section of said elongated body having a distal end face with a first female opening that seats said first post;
    said curved distal section of said elongated body having a proximal end face with a second female opening that seats said second post.

16. The reconfigurable suture needle as claimed in claim 10, further comprising:

said curved proximal section having a proximal end with a suture attachment end;

said curved distal section having a distal end with a tissue penetrating end.

17. A reconfigurable suture needle comprising:
an elongated body having a curved proximal section with a suture attachment end and a curved distal section with a tissue penetrating end;
a joint interconnecting a distal end of said curved proximal section and a proximal end of said curved distal section, wherein said joint enables said curved proximal section and said curved distal section to rotate relative to one another for transforming said elongated body between a first configuration having a higher profile and a second configuration having a lower profile;
a suture thread secured to the suture attachment end of said curved proximal section.

18. The reconfigurable suture needle as claimed in claim 17, wherein said elongated body of said reconfigurable suture needle has a semi-circular shape when in the first configuration and a wave shape when in the second configuration.

19. The reconfigurable suture needle as claimed in claim 18, wherein the wave shape of said elongated body when in the second configuration comprises a sine wave shape.

20. The reconfigurable suture needle as claimed in claim 17, wherein each of said curved proximal and distal sections of said elongated body defines about one-quarter (¼) of a circle.

* * * * *